(12) United States Patent
Manion et al.

(10) Patent No.: US 6,384,076 B1
(45) Date of Patent: May 7, 2002

(54) INHIBITION OR ERYTHROCYTE SICKLING BY N-L-ALPHA-ASPARTYL-L-PHENYLALANINE 1-METHYL ESTER

(75) Inventors: Carl V. Manion; Allen B. Edmundson, both of Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/787,994
(22) PCT Filed: Sep. 25, 1999
(86) PCT No.: PCT/US99/22268
§ 371 Date: Mar. 22, 2001
§ 102(e) Date: Mar. 22, 2001
(87) PCT Pub. No.: WO00/18418
PCT Pub. Date: Apr. 6, 2000

Related U.S. Application Data
(60) Provisional application No. 60/101,876, filed on Sep. 25, 1998.

(51) Int. Cl.[7] .............................. A61K 35/05; A61P 7/00
(52) U.S. Cl. ......................................... 514/542; 560/41
(58) Field of Search ............................. 560/41; 514/542

(56) References Cited

U.S. PATENT DOCUMENTS

| | | | |
|---|---|---|---|
| 5,177,208 A | 1/1993 | Wilburn | 544/277 |
| 5,629,285 A | 5/1997 | Black et al. | 514/2 |

FOREIGN PATENT DOCUMENTS

| | | | |
|---|---|---|---|
| WO | 9813062 | 4/1998 | A61K/38/05 |

OTHER PUBLICATIONS

Aluoch, J.R. "The Treatment of Sickle Cell Disease. A Historical and Chronological Literature Review of the Therapies Applied Since 1910," Tropical and Geographical Medicine 36:SI–26 (1984).

Carache, S. and Davies, S. "Teaching Both the Management and the Molecular Biology of Sickle Cell Disease," Academic Medicine 66:748–749 (1991).

Daland, G.A. and Castle, W.B. "A Simple and Rapid Method for Demonstrating Sickling of the Red Blood Cells: The Use of Reducing Agents," Journal of Laboratory and Clinical Medicine 33:1082–1088 (1948).

Dean, J. and Schechter, A.N. "Sickle Cell Anemia: Molecular and Cellular Bases of Therapeutic Approaches," The New England Journal of Medicine 299:752–763 (1978).

Dean, J. and Schechter, A.N. "Sickle Cell Anemia: Molecular and Cellular Bases of Therapeutic Approaches," The New England Journal of Medicine 299:804–811 (1978).

Dean, J. and Schechter, A.N. "Sickle Cell Anemia: Molecular and Cellular Bases of Therapeutic Approaches," The New England Journal of Medicine 299:863–870 (1978).

Edmundson, A.B. and Manion, C. V. "Treatment of Osteoarthritis with Aspartame," Clinical Pharmacology & Therapeutics 63:580–593 (1998).

Embury, S.H. "The Clinical Pathophysiology of Sickle Cell Disease," Annual Reviews of Medicine 37:361–376 (1986).

(List continued on next page.)

Primary Examiner—Bruck Kifle
Assistant Examiner—Rao Uppu
(74) Attorney, Agent, or Firm—Sidley Austin Brown & Wood

(57) ABSTRACT

It has now been found that N-L-alpha-aspartyl-L-phenylalanine 1-methyl ester (APM) exhibits antisickling properties. In vitro testing verified that APM significantly lowered the frequency of sickling of red blood cells from each of twelve pediatric aged patients being treated for sickle-cell anemia by exchange transfusion. Sickling was also inhibited in an "index" patient after oral administering of APM. These in vitro and in vivo results identify APM as a therapeutic agent for the family of sickle cell molecular diseases.

15 Claims, 11 Drawing Sheets

OTHER PUBLICATIONS

Friedman, M.J. and Trager, W. "The Biochemistry of Resistance to Malaria," Scientific American 244: 154–164 (1981).

Ingram, V.M. "A Specific Chemical Difference Between the Globins of Normal Human and Sickle–Cell Anaemia Haemoglobin," Nature 178: 792–794 (1956).

Manion, C. V., et al. "Sickle Cell Disease and Aspartame," Clinical Pharmacology and Therapeutics 65(2) Feb. 1999 (1999–2002) p. 194 XP000891777.

Murayama, M. "Molecular Mechanism of Red Cell Sickling," Science 153: 145–149 (1966).

Oliveri, N.F. and Vichinsky, E.P. "Hydroxyurea in Children with Sickle Cell Disease: Impact on Splenic Function and Compliance with Therapy," Journal of Pediatric Hematology / Oncology 20:26–31 (1998).

Padlan, E.A. and Love, W.E. "Refined Crystal Structure of Deoxyhemoglobin S," The Journal of Biological Chemistry 260:8280–8291 (1985).

Pauling, et al. "Sickle Cell Anemia, a Molecular Disease," Science 110: 543–548 (1949).

Pollack, et al, "Emergency Department Analgesia Without Narcotics for Adults with Acute Sickle Cell Pain Crisis: Case Reports and Review of Crisis Management," Journal of Emergency Medicine 9: 445–452 (1991).

Ranney, H.M. "Sickle Cell Disease," Blood 39: 433–439 (1972).

Rodgers, et al. "Pairings and Polarities of the 14 Strands in Sickle Cell Hemoglobin Fibers," Proceedings of the National Academy of Sciences USA 84: 6157–6161 (1987).

Scott–Conner, C.E. and Brunson, C.D. "The Pathophysiology of the Sickle Hemoglobinopathies and Implications for Perioperative Management," American Journal of Surgery 168:268–274 (1994).

Serjeant, G.B. "Chronic Transfusion Programmes in Sickle Cell Disease: Problem or Panacea?" British Journal of Haematology 97:253–255 (1997).

Selekman, J. "Update: New Guidelines for the Treatment of Infants with Sickle Cell Disease," Pediatric Nursing 19:600–605 (1993).

Wright, D.J. and Jenkins, D.E. "Simplified Method for Estimation of Serum and Plasma Viscosity in Multiple Myeloma and Related Disorders," Blood 36: 516–522 (1970).

INHIBITION OR ERYTHROCYTE SICKLING BY N-L-ALPHA-ASPARTYL-L-PHENYLALANINE 1-METHYL ESTER

This application is a 371 of PCT/US99/22268 filed Sep. 25, 1999, which claims benefit of U.S. provisional application Ser. No. 60/101,876 filed Sep. 25, 1998.

TECHNICAL FIELD OF INVENTION

The present invention relates to the treatment of sickle cell disease with N-L-alpha-aspartyl-L-phenylalanine 1-methyl ester.

BACKGROUND OF THE INVENTION

Under low oxygen tension, sickle cell deoxyhemoglobin (HbS) forms multi-stranded fibers (Rodgers, et al. 1987. Proc Natl Acad Sci USA 84:6157–6161; Eaton, W. A. and Hofrichter, J. 1990. Adv Protein Chem 40:63–279) that force a red blood cell (RBC) into a crescent (sickle) shape (Carache, S. and Davies, S. 1991. Acad Med 66:748–74). In 1949, Pauling et al. demonstrated that HbS was electrophoretically distinct from normal human adult hemoglobin (HbA) and coined the name molecular disease to describe the pathological effects of HbS (Pauling, et al. 1949. Science 110:543–548). Seven years later, Ingram (Ingram, V. M. 1956. Nature 178:792–794) reported that HbS differed from HbA by the substitution of valine for glutamic acid in position 6 of the β chain. This hydrophobic for polar substitution occurs on the surface of the three-dimensional structure of HbS on the first (A) α-helix (Padlan, E. A. and Love, W. E. 1985. J Biol Chem 260:8280–8291). It creates a sticky site which is covered by a complementary (acceptor) crevice between the E and F helices in the β chain of an antiparallel Hb molecule in the fibril. Key contact residues in the acceptor site are phenylalanine 85 and leucine 88 from the F helix. Each β chain thus contains a donor and acceptor site which together interact with two other offset Hb molecules, the key condensation events in producing double stranded helical stacks of indefinite length. As the strands of hemoglobin molecules stack together they, continue to elongate and stretch the normally round, flexible RBC into an inflexible sickle or spiculated shape.

Physiologically, the sickled RBCs impair blood flow, enhance hypoxia and accentuate the production of more sickling (Embury, S. H. 1986. Ann Rev Med 37:361–376). The HbS gene is present in about 8–9% of African Americans (Schneider, et al. 1976. Blood 48:629). If homozygous for the gene, a patient shows the severe symptoms of "sickle cell disease" such as anemia, hemolysis, severe muscle pain, thrombotic complications, and even sudden exertional death. A heterozygous individual has "sickle cell trait" with milder symptoms and more infrequent crises. The gene is believed to have been preserved in successive generations because RBCs containing HbS appear to promote survival in endemic malarial regions of Africa, Asia and European countries on the Mediterranean Sea (Allison, A. C. 1956. Scientific American 195:87–94; Friedman, M. J. and Trager, W. 1981. Scientific American 244:154–164).

Research for therapeutic agents known to delay the onset of sickle cell gelation without introducing unacceptable side effects has been ongoing for many years. (Murayama, M. 1966. Science 153:145–149; Dean, J. and Schechter, A. N. 1978. New Engl J Med 299:804–811; Dean, J. and Schechter, A. N. 1978. New Engl J Med 299:863–870; Dean, J. and Schechter, A. N. 1978. New Engl J Med 299:752–763). No significant approach has been advanced for the treatment of sickling phenomena (Ranney, H. M. 1972. Blood 39:433–439; Aluoch, J. R. 1984. Trop Geogr Med 36:SI-26; Serjeant, G. R. 1997. Br J Haematol 97:253–255; Olivieri, N. F. and Vichinsky, E. P. 1998. J Pediatr Hematol Oncol 20:26–31), although there are many stimulating research approaches and hydroxyurea has some effect. (Dickerson, R. E. and Geis, I. Hemoglobin: Structure, Function, Evolution, and Pathology. Benjamin/Cummings Publishing Co., Menlo Park, 1st Park, ed., 1983). Clinical management of a sickle-cell crisis is usually described as supportive, using fluids for hydration (Scott-Conner, R. E. and Brunson, C. D. 1994. Am J Surg 168:268–274), oxygen for alleviation of hypoxic sickling and analgesics for pain relief (Pollack, et al. 1991. J Emerg Med 9:445–452). Though often effective, even exchange transfusion remains controversial as preventive therapy (Selekman, J. 1993. Pediatr Nurs 19:600–605).

U.S. Pat. No. 5,654,334 discloses APM as a pain reliever which is especially effective in relieving pain associated with osteoarthritis and multiple sclerosis. Further, International Application WO 97/00692 discloses APM as an antipyretic. In a clinical trial, APM was demonstrated to alleviate the pain and inflammation of osteo- and mixed osteo- and rheumatoid arthritis by an unknown mechanism (Edmundson, A. B. and Manion, C. V. 1998. Clin Pharm Therap 63:580–593). Additionally, International Application WO 98/13062 discloses the efficacy of APM in the treatment of a disease affected by the presence of TNFα, particularly arthritis and rheumatoid arthritis. U.S. Pat. No. 5,629,285 discloses sickle cell anemia as one of numerous diseases in which the overproduction or unregulated production of TNFα has been implicated It has now been found that APM displays binding behavior with HbS resulting in a modified HbS molecule useful for treatment of the sickle cell family of diseases.

SUMMARY OF THE INVENTION

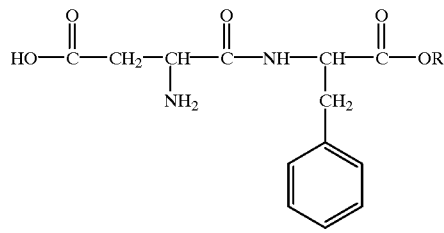

The present invention relates to the use of the compound where R is $CH_3$ or an alkyl which allows transport of the compound across the red blood cell membrane to prepare a pharmaceutical composition useful for effecting a reduction in sickle cells in a mammal. The preferred compound used to prepare the pharmaceutical composition is N-L-alpha-aspartyl-L-phenylalanine 1-methyl ester (R=$CH_3$). In one embodiment, these compounds are used to prepare a pharmaceutical composition useful for treating sickle cell disorders.

In another aspect the present invention relates to a pharmaceutical preparation in dosage unit form adapted for administration to obtain an antisickling effect in red blood cells, comprising, per dosage unit, an antisickling effective non-toxic amount of a compound comprising

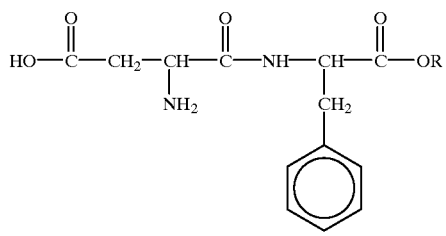

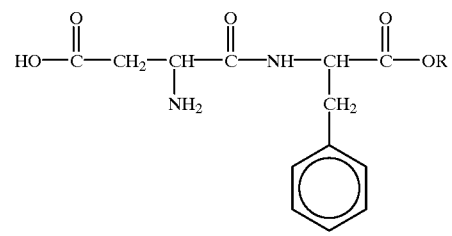

where R is $CH_3$ or an alkyl which allows transport of the compound across the red blood cell membrane and a pharmaceutical carrier. Preferably, the compound comprises N-L-alpha-aspartyl-L-phenylalanine 1-methyl ester (R=$CH_3$).

In another aspect, the present invention relates to a pharmaceutic dosage form for use as an antisickling agent comprising the compound

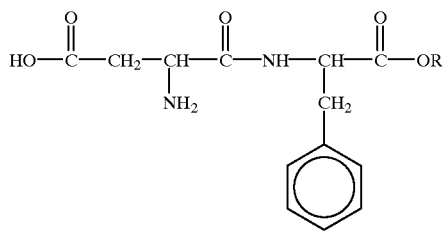

where R is $CH_3$ or an alkyl which allows transport of the compound across the red blood cell membrane, wherein the dosage form comprises preferably from about 1.5 milligrams to about 6 milligrams per kilogram body weight of the compound. More preferably, the dosage form comprises about 6 milligrams per kilogram body weight of the compound, preferably to be administered twice a day. The preferred dosage form comprises N-L-alpha-aspartyl-L-phenylalanine 1-methyl ester (R=$CH_3$).

In another aspect, the present invention relates to a pharmaceutical dosage form comprising an active antisickling ingredient, wherein the active antisickling ingredient comprises the compound

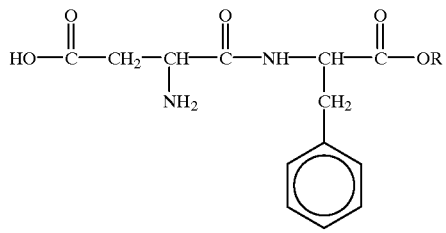

where R is $CH_3$ or an alkyl which allows transport of the compound across the red blood cell membrane. The effective amount of the compound in the active ingredient is preferably from about 1.5 milligrams to about 6 per kilogram body weight. More preferably, the effective amount of the compound in the active ingredient is about 6 milligrams per kilogram body weight, preferably to be administered twice a day. The preferred active ingredient comprises N-L-alpha-aspartyl-L-phenylalanine 1-methyl ester (R=$CH_3$).

In another aspect, the present invention relates to the use of the compound where R is $CH_3$ or an alkyl which allows transport of the compound across the red blood cell membrane to produce an antisickling effect in red blood cells in vitro. The preferred effective amount of the compound is from about 1 milligrams to about 2 milligrams per milliliter. Preferably, the compound is N-L-alpha-aspartyl-L-phenylalanine 1-methyl ester (R=$CH_3$).

In yet another aspect, the present invention relates to a formulation for treatment of red blood cells suspected to contain sickle cells, the formulation comprising the compound

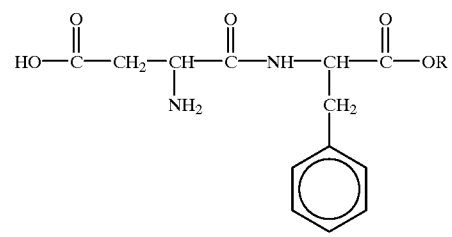

where R is $CH_3$ or an alkyl which allows transport of the compound across the red blood cell membrane and calcium. Preferably, the formulation comprises N-L-alpha-aspartyl-L-phenylalanine 1-methyl ester (R=$CH_3$).

In yet another aspect, the present invention relates to a method for reducing the number of sickle cells relative to the number of normal red blood cells in a patient blood sample from the time of collection of the blood sample from the patient to a second time of laboratory analysis, comprising the steps of: (a) collecting a blood sample from a patient having a sickle cell disorder, wherein red blood cells in the blood sample have a predisposition to sickle; and (b) adding to the blood sample at the time of collection an effective amount of a composition comprising the compound

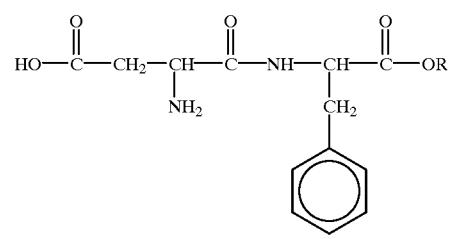

where R is $CH_3$ or an alkyl which allows transport of the compound across the red blood cell membrane, wherein the effective amount causes a reduction in the number of sickle cells relative to the number of normal red blood cells in a patient blood sample at the time of laboratory analysis. Preferably, the compound in the composition is N-L-alpha-aspartyl-L-phenylalanine 1-methyl ester (R=$CH_3$).

In yet another aspect, the present invention relates to a method of treatment of sickle cell disease in a patient by administration of an effective amount of a composition comprising the compound

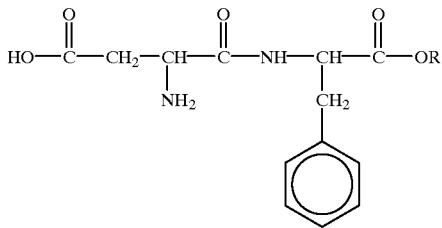

where R is $CH_3$ or an alkyl which allows transport of the compound across the red blood cell membrane, wherein the treatment results in a reduction of the number of sickle cells relative to the number of normal cells in the patient's blood. A preferred effective amount of the compound is from about 1 milligrams to about 6 milligrams kilograms body weight. A more preferred effective amount of the compound is about 6 milligrams of per kilograms body weight. Preferably, the compound in the composition is N-L-alpha-aspartyl-L-phenylalanine 1-methyl ester (R=$CH_3$). The treatment is preferably administered daily. Preferably, the treatment is administered orally.

Figure 11:
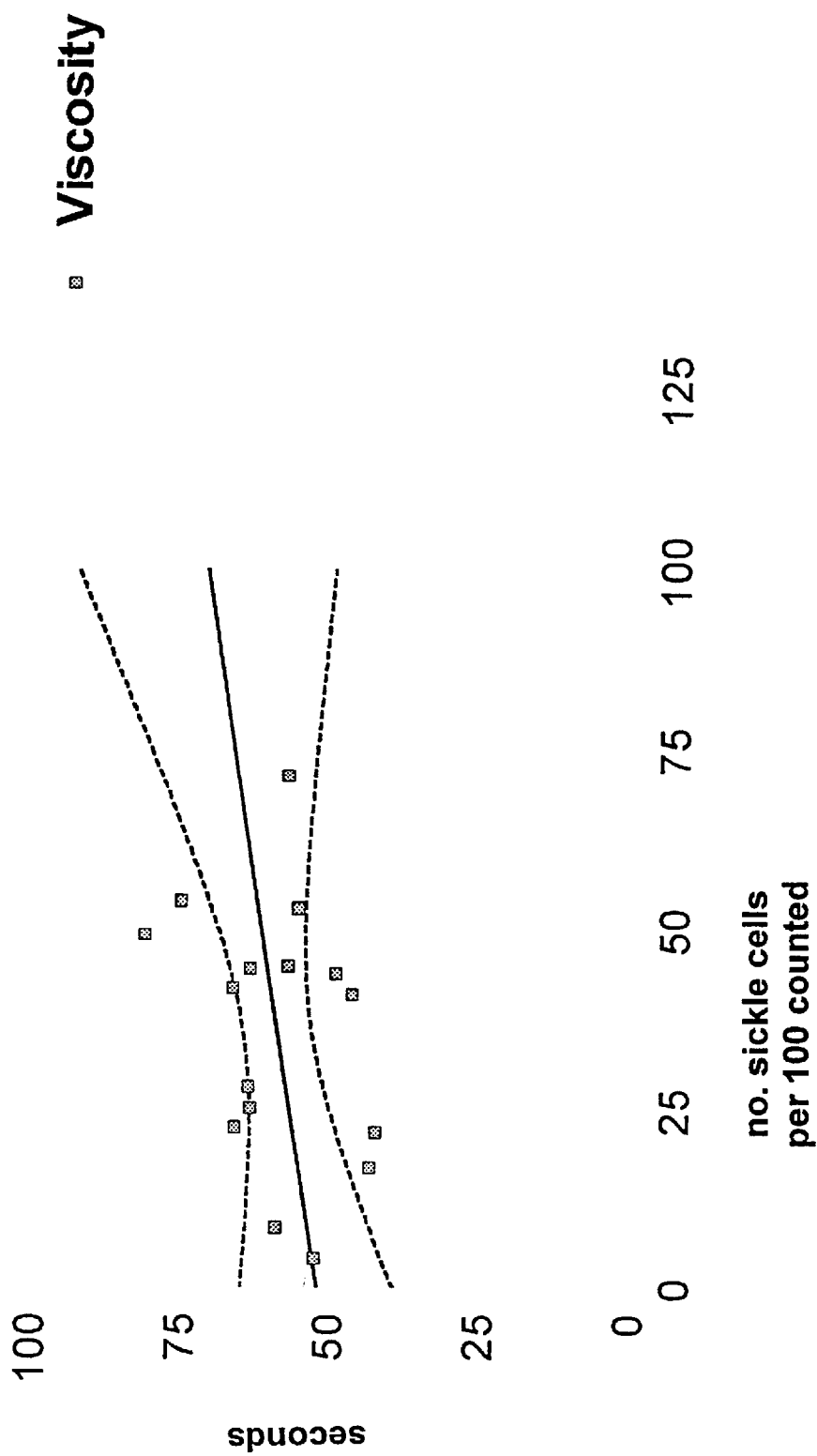

FIG. 11 is a graph depicting the correlation of sickle cell count to viscosity, demonstrating a linearly proportional correlation, i.e., as the number of sickle cells per total number of cells counted increases, viscosity also increases.

DETAILED DESCRIPTION

It has now been found that N-L-alpha-aspartyl-L-phenylalanine 1-methyl ester (APM) interacts with the HbS molecule to the extent that the stacking of the HbS molecules within the RBC is significantly altered, leading to a reduction in the capacity of RBCs containing HbS to sickle with hypoxemia. Upon administration of an effective amount of APM, patients having genetic diseases of the sickle cell family experience a reduction in the number of sickle cells relative to the number of normal cells within one hour of administration, demonstrating APM's medicinal qualities beneficial in the treatment of sickle cell diseases.

A preferred effective amount of APM which can effect a reduction in sickle cells after one dose is from about 1 milligrams to about 6 milligrams per kilogram body weight. A more preferred range is from about 3 milligrams to about 6 milligrams per kilogram body weight. Most preferred is about 6 milligrams per kilogram body weight. The dosage can be repeated over time for continued relief, preferably at 6 milligrams every 12 hours.

APM can be administered orally, parenterally, intraperitoneally, or sublingually. It can be administered via ingestion of a food substance containing APM in a volume sufficient to achieve therapeutic levels. Alternatively, it can be enclosed in capsules, compressed into tablets, microencapsulated, entrapped in liposomes, in solution or suspension, alone or in combination with a substrate immobilizing material such as starch or poorly absorbable salts. Pharmaceutically compatible binding agents and/or adjuvant materials can be used as part of a composition. Tablets or capsules can contain any of the following ingredients, or compounds of similar nature: a binder such as microcrystalline cellulose, gum tragacanth or gelatin; an excipient such as starch or lactose; an integrating agent such as alginic acid; corn starch; a lubricant such as magnesium stearate; a glidant such as colloidal silicon dioxide; and additional sweetening and flavoring agents. When a capsule form is used the liquid carrier such as a fatty oil may be used. Capsules and tablets can be coated with sugar, shellac and other enteric agents as is known. APM can also be in a controlled-release formulation.

With the exception of patients suffering from phenylketonuria, APM is considered as a GRAS (generally regarded as safe) substance. APM is commercially available, e.g., as ASPARTAME™ (G. D. Searle & Company, Chicago, Ill.). Its preparation is also disclosed in U.S. Pat. No. 3,492,131. While APM is preferred, it is believed that a derivative of APM which can cross the RBC membrane and interact with the HbS molecule to the extent that the stacking of the HbS molecules is significantly altered can also be administered as an effective treatment for sickle cell disease. Exemplary derivatives include but are not limited to the ethyl, propyl and butyl esters, and the derivatives should maintain the sweetening property of the dipeptide. Such derivatives, which can be determined using the monitoring methods provided in the examples below, are considered to fall within the scope of this invention. It is to be understood that "APM" used herein refers to N-L-alpha-aspartyl-L-phenylalanine 1-methyl ester or its derivative as defined above.

The effectiveness of APM treatment for sickle cell diseases can be monitored by several methods. Routine laboratory screening methods known in the art for testing for sickle cell disorders can be used. For example, normal RBCs are more soluble than sickled RBCs, and the observation of an increased solubility of RBCs in blood samples taken from a patient suffering from a sickle cell disease is indicative of effective APM treatment. Use of a metabisulfite slide test on heparinized blood samples as presented in Example 1 can also be used, wherein a decrease in the number of sickle cells relative to normal cells indicates effective APM treatment. This metabisulfite screening method does not distinguish sickle cell trait (heterozygous for HbS) from sickle cell disease (homozygous for HbS), because all RBCs containing HbS will sickle. As presented in Example 4, a monitoring method based on the fact that the viscosity of blood from patients with sickle cell diseases decreases when treated with APM can also be used. This monitoring procedure can be used to distinguish sickle cell disease from sickle cell trait, although hemoglobin electrophoresis is more commonly used.

Sickling of RBCs in a patient sample changes both the physical and chemical characteristics of the sample over time. There are advantages to reducing the degradation caused by sickling for certain applications, particularly crisis. Because of its antisickling properties, APM can be used as a stabilizing agent to reduce sickling of RBCs in whole blood and RBC specimens from the time of collection of the whole blood specimens from the patient until the time the specimen is either analyzed by the laboratory or utilized in in vitro experimentation. An effective amount of APM can be added to a transport container either before or immediately after the blood sample is added to the transport container.

EXAMPLE 1
Reduction of Sickle Cells in in vitro Blood Samples

In an in vitro study, APM was shown to be transported across the RBC membrane and to effect a decrease in the sickling of cells in blood samples taken from patients suffering from sickle cell disorders.

Blood was drawn from twelve patients of pediatric age who were being treated by phlebotomy and exchange transfusion for their sickling disorders. Blood samples from each patient were drawn directly into heparin tubes, stored in a refrigerator at approximately 10° C., and routinely tested within 36 hours of collection. Some samples were rechecked or reanalyzed within a week of collection, and the effects on sickle hemoglobin was still present with counted values similar to those obtained within 36 hours.

Normal blood devoid of HbS was used as a control. For each heparinized patient blood sample and the normal blood control, three experimental samples were prepared containing 0.25 milliliters of normal saline and 0.25 milliliters of blood and then treated as follows: (1) one was left untreated; one was treated with 1 milligram APM; and (3) one was treated with 2 milligrams APM. All experimental samples were stored in a refrigerator at approximately 10° C. for one hour prior to testing to allow time for the APM to be absorbed by the RBCs.

Using metabisulfite to reduce HbS to the deoxy form (Daland, G. A. and Castle, W. B. 1948. *J Lab Clin Med* 33:1082–1088; Nelson, D. A. In *Todd-Sanford-Davidsohn Clinical Diagnosis by Laboratory Methods,* J. B. Henry, ed. (W. B. Saunders Co., Philadelphia, 1979, vol. 1, p. 1020), a sickling test was run on each experimental sample. The sickling inducing agent was prepared fresh daily as follows: 10 milligrams metabisulfite in 1 milliliter isotonic saline. Multiple test slides were prepared for each experimental sample by adding 3 drops of the metabisulfite inducing agent and 1 drop of the experimental sample onto the surface of a glass slide, placing a coverslip over the sample, and sealing the coverslip with a petroleum jelly bead to prevent oxygen from entering the sample. Photomicrographs were taken with a phase contrast microscope at 400 magnification at 0, 30, and 120 minutes after slide preparation, and the results were obtained from the photomicrographs as the number of sickle cells per 100 cells counted.

To account for natural or non-induced sickling of the experimental samples, a baseline sickling count was increasing APM concentration. Analysis of variance was statistically significant at $p<0.00004$. In the photomicrographs, relatively small numbers of sickle cells were observed in the APM-treated slides. Moreover, in contrast to the uniform appearance of normal biconcave RBCs or sickle cells, the APM-treated cells developed uneven hemoglobin patches with sharply defined borders, indicating the presence of irregular, small bundles of sickled fibers which were prevented by APM from becoming sufficiently large enough to deform the cells into the sickle shape.

Figure 2:
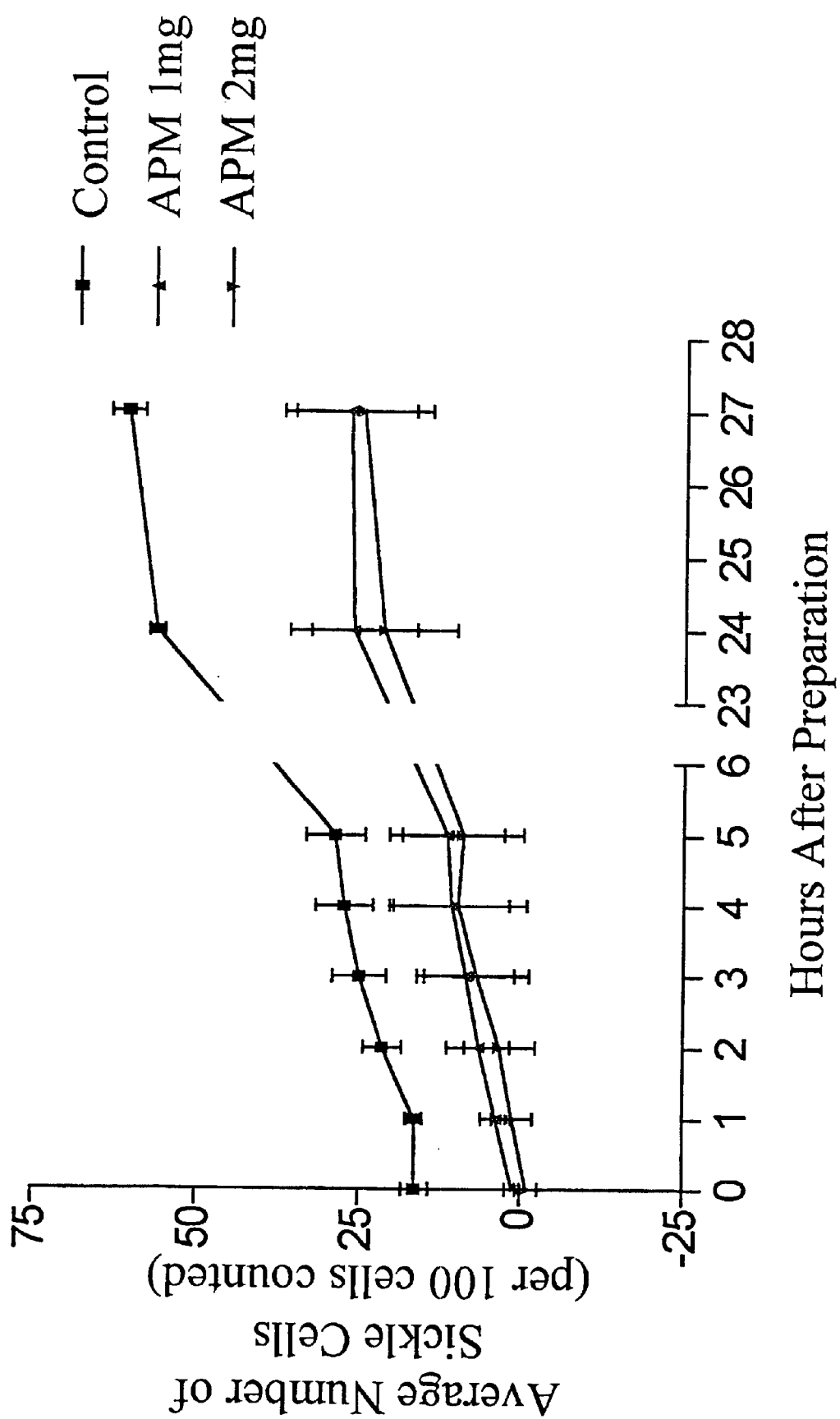
FIG. 2 is a graph depicting the duration of APM effect on sickling of RBCs. Blood samples and slides were prepared according to the methods given in Example 1, and results were measured as the average numbers of sickle cells per 100 cells counted at 0, 1, 2, 3, 4, 5, 24, and 27 hours after slide preparation. The data from the 12 patients is combined into treatment groups (control, solid square; 1 milligram APM, upward pointing triangle; 2 milligram APM, downward pointing triangle).

A timeline for APM effect was made by repeating the experiment given above with cell counts obtained at 0, 1, 2, 3, 4, 5, 24, and 27 hours post-metabisulfite induction. The results are presented in FIG. 2 as combined APM timelines for each treatment method. The antisickling effect of APM in vitro lasted for at least 27 hours. During this period, the rate of sickling in the APM treated

TABLE I

Sickle Cell Counts from Twelve Pediatric Patients with Known HbS Syndrome
Number of Cells Sickled per Hundred Counted

| Time | Patient | | | | | | | | | | | | |
|---|---|---|---|---|---|---|---|---|---|---|---|---|---|
| (MIN) | 1 | 2 | 3 | 4 | 5 | 6 | 7 | 8 | 9 | 10 | 11 | 12 | Mean |
| Control | | | | | | | | | | | | | |
| 0 | 8.5 | 8.5 | 10.0 | 20.0 | 15.5 | 4.0 | 21.5 | 20.5 | 12.5 | 22.5 | 13.0 | 18.5 | |
| 30 | 13.5 | 10.5 | 12.5 | 22.5 | 18.0 | 9.5 | 27.5 | 21.0 | 13.5 | 23.5 | 12.0 | 22.0 | |
| 120 | 16.5 | | 15.5 | 22.5 | 20.0 | 21.5 | 33.5 | 27.5 | 15.5 | 29.5 | 18.0 | 25.5 | |
| Avg | 12.8 | 9.5 | 12.7 | 21.7 | 17.8 | 11.7 | 27.5 | 23.0 | 13.8 | 25.2 | 14.3 | 22.0 | 17.7 |
| APM 1 mg | | | | | | | | | | | | | |
| 0 | 2.5 | 2.0 | 2.5 | 9.5 | 9.5 | 1.5 | 2.0 | −1.0 | 1.5 | 1.0 | 0.5 | 0.0 | |
| 30 | 1.5 | 3.5 | 3.0 | 10.5 | 9.0 | 4.5 | 3.5 | −0.5 | 2.5 | 2.0 | −1.0 | 6.0 | |
| 120 | 2.5 | | 3.0 | 12.0 | 11.0 | 3.5 | 4.0 | 0.5 | 1.5 | 3.5 | 1.0 | 21.0 | |
| Avg | 2.2 | 2.8 | 2.8 | 10.7 | 9.8 | 3.2 | 3.2 | −0.3 | 1.8 | 2.2 | 0.2 | 9.0 | 4.0 |
| APM 2 mg | | | | | | | | | | | | | |
| 0 | 2.5 | 1.0 | 2.0 | 6.5 | 8.5 | 0.5 | 1.0 | −5.5 | 0.5 | 0.0 | 0.0 | 2.0 | |
| 30 | 2.0 | 1.5 | 2.0 | 5.0 | 8.5 | 2.0 | 0.5 | −6.5 | 0.5 | 1.0 | −0.5 | 6.0 | |
| 120 | 2.5 | | 5.0 | 2.0 | 9.5 | 2.0 | 1.0 | −6.5 | −0.5 | 0.5 | −0.5 | 19.0 | |
| Avg | 2.3 | 1.3 | 3.0 | 4.5 | 8.8 | 1.2 | 0.8 | −6.2 | 0.0 | 0.5 | −0.3 | 9.0 | 2.1 |

Heparinized specimens of whole blood were treated with metabisulfite to induce sickling before and after exposure to APM. Number of sickle cells observed in the specimens before metabisulfite additions were subtracted from the totals, resulting in some values with negative numbers.

obtained for each heparinized patient blood sample and the normal blood control. Slides were prepared by adding 3 drops of saline and 1 drop of the experimental sample onto the surface of a glass slide, placing a coverslip over the sample, and sealing the coverslip with a petroleum jelly bead to prevent oxygen from entering the sample. Photomicrographs were taken with a phase contrast microscope at 400 magnification at 0, 30, and 120 minutes after slide preparation, and the results were obtained from the photomicrographs as the number of sickle cells per 100 cells counted. This number of sickle cells per 100 cells counted was considered the baseline sickling count and was subtracted from the cell counts obtained with the metabisulfite induced samples.

Figure 1:
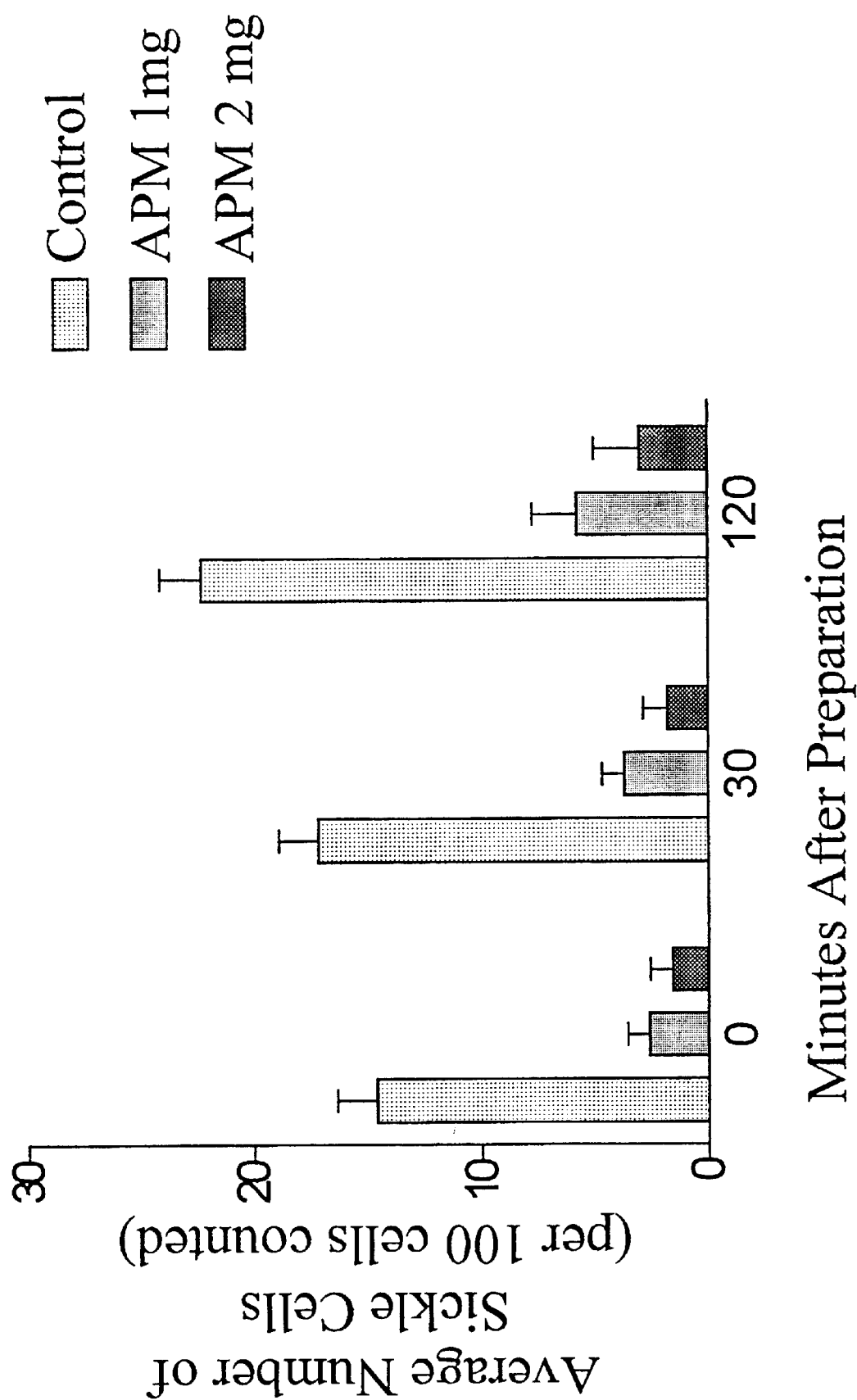
FIG. 1 is a graph depicting the proportion of sickle cells in the population of RBCs (erythrocytes) plotted against time in the absence of APM (Control) and in the presence of APM added in quantities of 1 and 2 mg. The blood samples and slides were prepared according to the methods given in Example 1. Results were measured as the average number of sickle cells per 100 cells counted over time after slide preparation, with the data from the 12 patients combined into treatment groups: control, 1 milligram APM, and 2 milligram APM. Standard error, bars of the mean values are shown for N=12 tested patients.

As shown in Table 1 and FIG. 1, after exposure to metabisulfite in the presence of APM, heparinized blood samples from all twelve patients contained fewer sickle cells than the controls. The effects of APM in reducing the number of sickle cells was immediate and increased with cells was significantly less than that in the controls. Thus, while sickling was not prevented by APM over time, its progression was limited over time.

Figure 3:
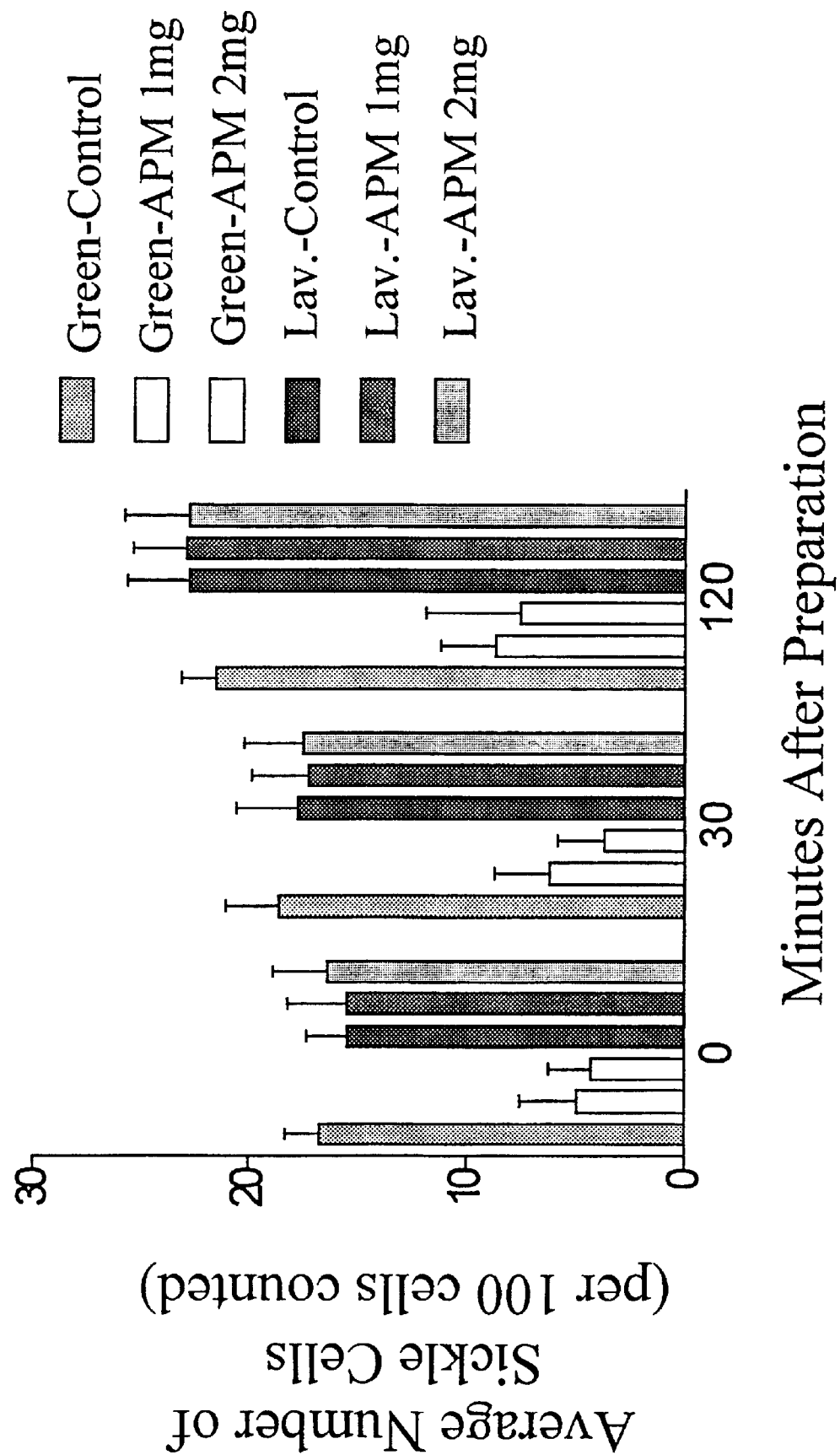
FIG. 3 is a graph depicting the proportion of sickle cells in the RBC population plotted against time in the absence of APM (Control) and in the presence of APM added in quantities of 1 and 2 milligrams with (Lav.) and without (Green) the addition of EDTA. The blood samples and slides were prepared according to the procedures given in Example 1. The results were measured as the average number of sickle cells per 100 cells counted at 0, 30 and 120 minutes after slide preparation, with the data from the 12 patients combined into treatment groups. In each grouping at 0, 30, and 120 minutes, the bars appear from left to right in the same order as the listings in the legend presented from top to bottom.

The effect of calcium ($Ca^{2+}$) on the effectiveness of APM was examined by repeating the experiment above with the addition of EDTA, a $Ca^{2+}$ chelating agent, to normal blood control and the patient experimental samples prior to testing. FIG. 3 illustrates the comparative heparin versus EDTA treatment of the blood. The addition of EDTA completely eliminated the antisickling effect of APM, a result indicating that APM does not pass the RBC membrane in the absence of $Ca^{2+}$. These results also demonstrate that the use of EDTA as an anticoagulant in screening tests will negatively bias conclusions of the effectiveness of APM which require $Ca^{2+}$ for transport across the RBC membrane. Moreover, the addition of a calcium salt to APM formulations useful for antisickling treatment as well as in vitro applications is desirable.

EXAMPLE 2
Reduction of Sickle Cells in vivo

The antisickling effect of APM was observed in heparinized blood samples taken from a female patient with sickle cell anemia.

During Week 1 of the study, blood samples were taken from the patient before and one hour after an orally administered dose of 60 milligrams APM. During Week 2, blood samples were taken from the patient before and one hour after an orally administered dose of 160 milligrams APM. The blood samples and slides were prepared according to the methods given in Example 1, and cell counts were taken at 0, 30, and 120 minutes post-induction.

Figure 4:
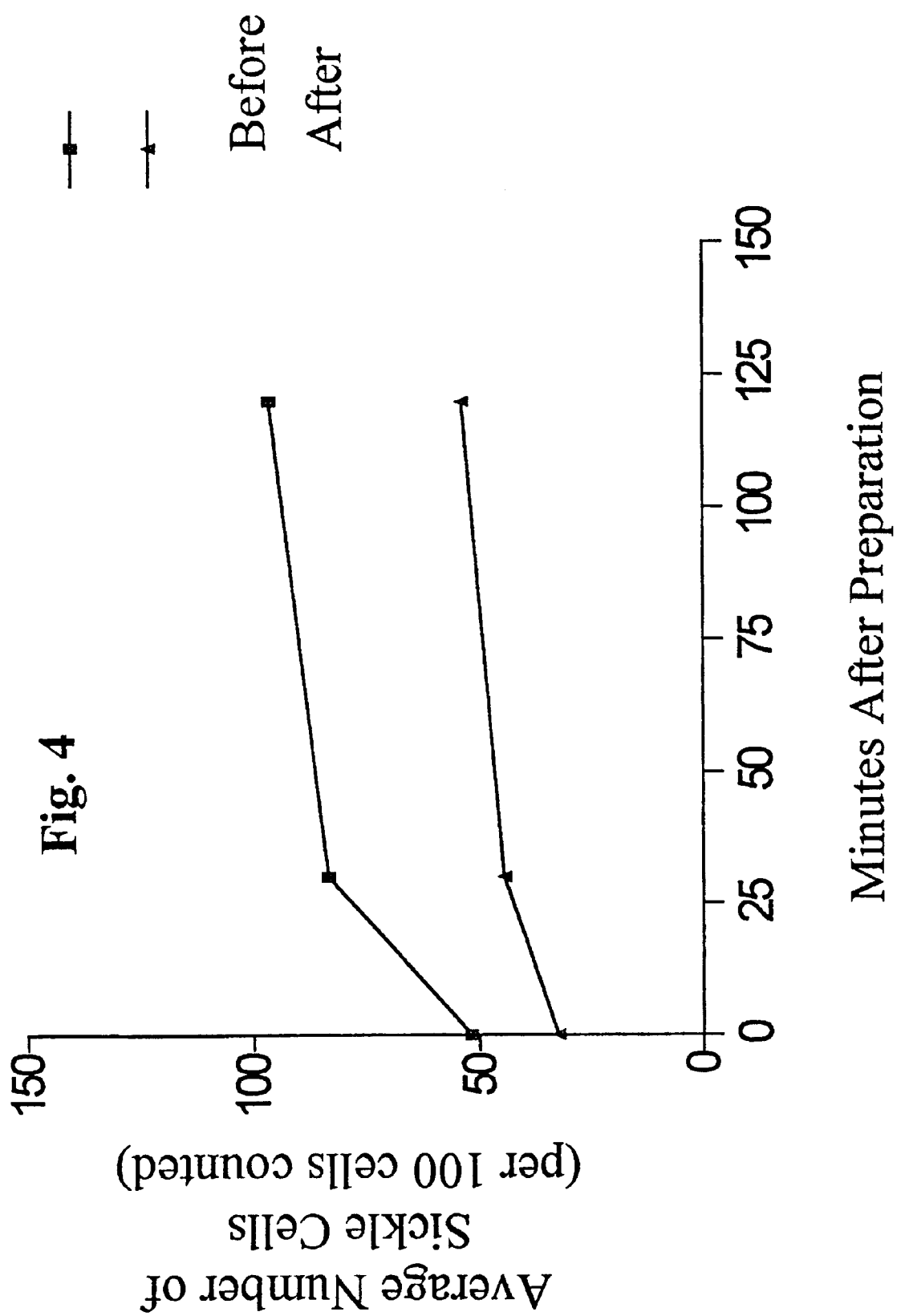
FIG. 4 is a graph illustrating the in vivo response of a patient with a known HbS syndrome to treatment with 60 milligrams APM. Heparinized blood specimens were obtained before (solid square) and 1 hour after (solid triangle) APM ingestion: The blood samples and slides were prepared according to the procedures given in Example 1. Results were measured as the average number of sickle cells per 100 cells counted over time after slide preparation.
Figure 5:
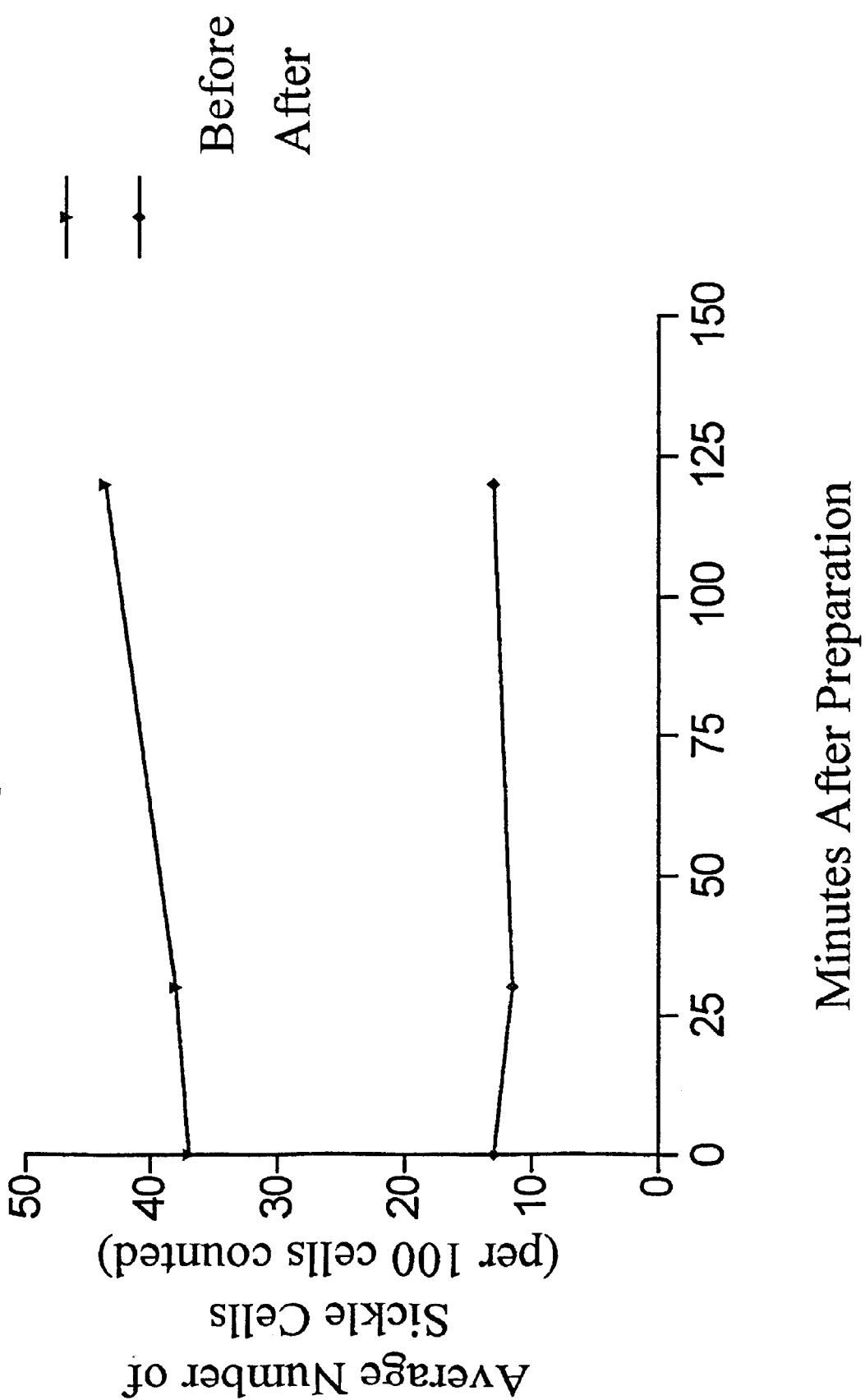
FIG. 5 is a graph depicting the in vivo response of patient with a known HbS syndrome to treatment with 160 milligrams APM. Heparinized blood samples were obtained before (solid triangle) and 1 hour after (solid diamond) APM ingestion. Blood samples and slides were made according to the procedures given in Example 1. Results were measured as the number of sickle cells per 100 cells counted over time after slide preparation.

The results of the study are given in FIGS. 4 and 5 for the 60 milligram and 160 milligram treatments, respectively. A decrease in the number of sickling RBCs relative to the control was observed after administration of the lower dosage, thereby confirming an antisickling response upon APM ingestion. At the higher 160 milligram dosage, the antisickling effect was proportionately larger than the effect observed with the 60 milligram dosage, indicating a significant dose response effect.

EXAMPLE 3
APM Dose-Response Study of Patients with Sickle Cell Disorders

A blinded study was conducted with 23 patients diagnosed with sickle cell disorders. Blood samples were obtained from the 23 patients having sickle cell disease (homozygous HgBss), sickle cell trait (heterozygous Hgbsc), or homozygous HbS with a β-thalassemia chain ("sbthal") before and after a blinded administration of APM at 1.5 (low dosage), 3 (medium dosage), or 6 (high dosage) milligrams per kilogram body weight. The patients' characteristics are presented in Table II.

Blood was drawn before and 120 minutes after treatment with 0, 1.5, 3, or 6 milligrams APM per kilogram body weight in a blinded fashion from the ten patients into heparin tubes, stored in a refrigerator at approximately 10° C. and routinely tested within 36 hours of collection.

Normal blood devoid of abnormal hemoglobin was used as a control. For each heparinized patient blood sample and the normal blood control, experimental samples were prepared containing 0.25 milliliters of normal saline and 0.25 milliliters of blood. Following the metabisulfite induction as given in Example 1, the number of sickle cells relative to the number of normal cells was obtained at 0, 30, 60, 120, 240, 480, and 1440 minutes post-induction.

Figure 6:
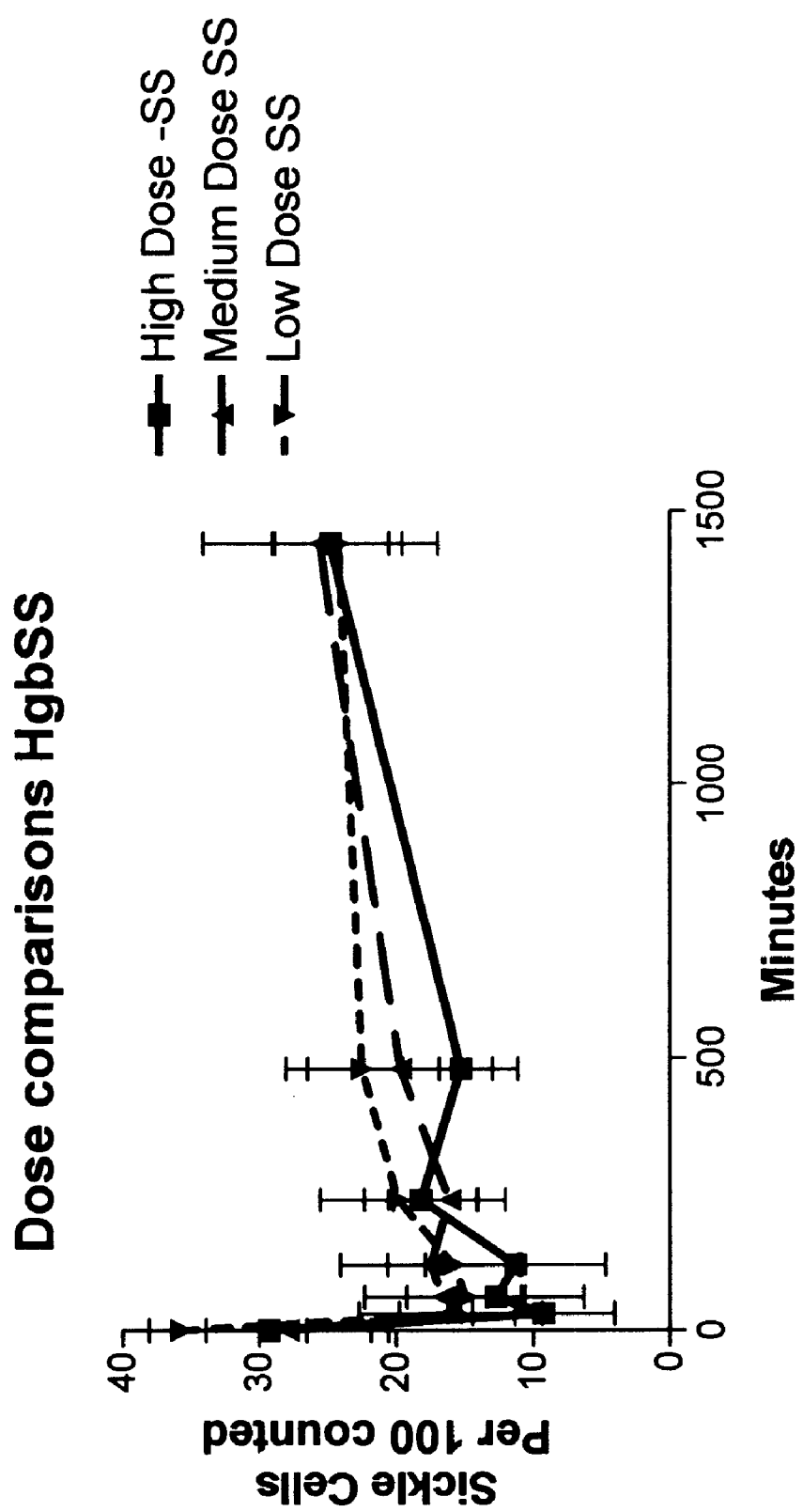
FIG. 6 is a graph depicting the dose comparisons over time for HgBss patients treated with 1.5 (low dosage; triangle pointing downward), 3 (medium dosage; triangle pointing upward), or 6 (high dosage; closed square) milligrams APM per kilogram body weight. Results are reported as the number of sickle cells per 100 cells counted taken at 0, 30, 60, 120, 240, and 1,440 minutes after blinded administration of APM.
Figure 7:
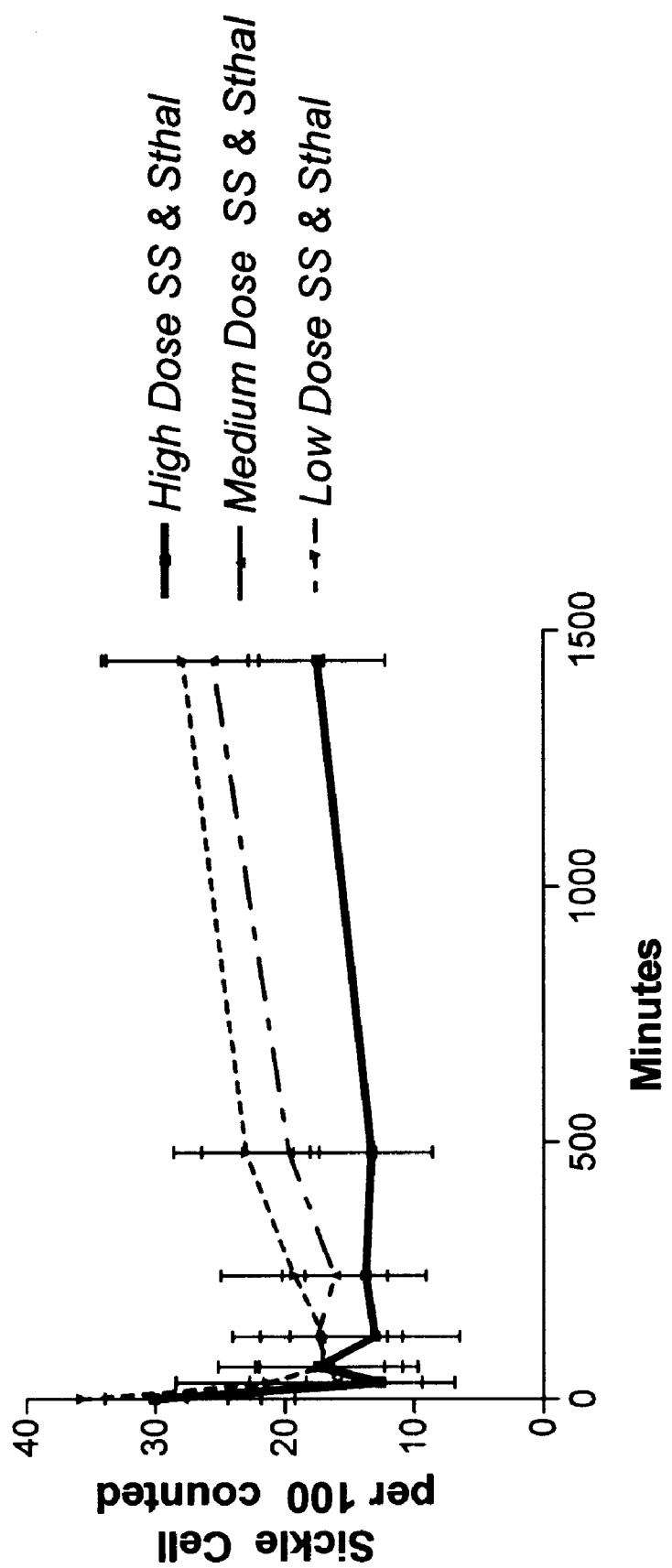
FIG. 7 is a graph depicting the dose comparisons over time for combination of HgBss and sbthal patients treated with 1.5 (low dosage; broken line with triangle pointing downward), 3 (medium dosage; broken line with triangle pointing upward), or 6 (high dosage; solid line with closed square) milligrams APM per kilogram body weight. Results are reported as the number of sickle cells per 100 cells counted taken at 0, 30, 60, 120, 240, and 1,440 minutes after blinded administration of APM.
Figure 8:
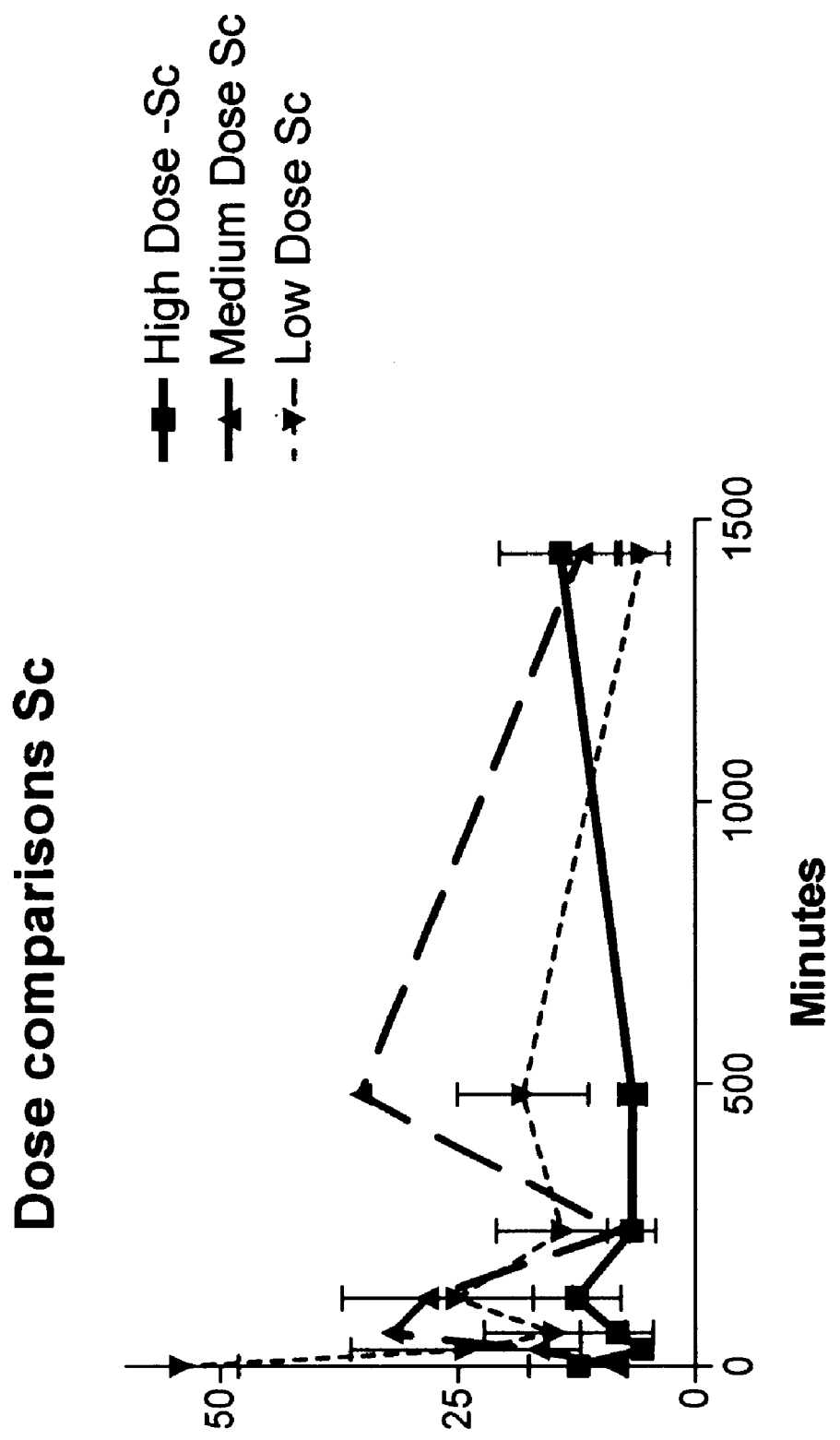
FIG. 8 is a graph depicting the dose comparisons over time for Hgbsc patients treated with 1.5 (low dosage; triangle pointing downward), 3 (medium dosage; triangle pointing upward), or 6 (high dosage; closed square) milligrams APM per kilogram body weight. Results are reported as the number of sickle cells per 100 cells counted taken at 0, 30, 60, 120, 240, and 1,440 minutes after blinded administration of APM.

The results of the study are presented as the number of sickle cells per 100 total cells counted over time. Dose comparisons for the combined HgBss patients, combined HgBss and sbthal patients, and combined Hgbsc patients are presented in FIG. 6, FIG. 7, and FIG. 8, respectively. A decrease in the number of sickling RBCs relative to the control was observed after administration of the lower dosage, thereby confirming an antisickling response upon APM ingestion (data not shown). At the higher dosage, the antisickling effect was proportionately larger than the effect observed with the medium dosage, and the antisickling effect of medium dosage was greater than the effect of the low dosage, indicating a significant dose-response effect. No dose-response effect was observed with Hgbsc.

TABLE II

Patient Characteristics for Dose-Response Study

| ID | Age | Sex | Disease[b] | Hgb | Hct | Dose[c] | ELECTROPHORESIS ss | f | a | c |
|---|---|---|---|---|---|---|---|---|---|---|
| TD[a] | 13 | m | ss | 7.6 | 25.4 | H | 100 | | | |
| AH[a] | 11 | f | ss | 6.1 | 23.3 | M | | | | |
| JC[a] | 13 | m | sbthal | 7.5 | 25.1 | L | 77.1 | 18 | | |
| TC[a] | 9 | f | sbthal | 7.9 | 25.6 | H | 64.5 | 32 | | |
| JU[a] | 4 | m | ss | 7.9 | 22.6 | M | 84.8 | 10.9 | | |
| LJ[a] | 4 | m | ss | 7.9 | 22.6 | L | | | | |
| TM[a] | 19 | f | sc | 10.3 | 30.2 | L | | | | |
| BB[a] | 39 | f | sc | 11.5 | 39 | H | | | | |
| CH[a] | 52 | f | sc | 8 | 26 | M | | | | |
| LW[a] | 3 | f | ss | 7.4 | 24 | M | | | | |
| DM | 19 | m | ss | 9.8 | 29.4 | H | 83.2 | 13.1 | | |
| CM | 21 | m | ss | 9.9 | 29.3 | M | 58.4 | | 29.4 | |
| CA | 14 | m | ss | 7.5 | 21.1 | L | 92.8 | 1.9 | | |
| QR | 6 | m | ss | 7.1 | 20.2 | M | 90.1 | 5.1 | | |
| OF | 2 | f | ss | 9.6 | 29 | L | 75 | 20.5 | | |
| DA | 4 | f | ss | 7.12 | 21.3 | H | 67 | 12.7 | 18.4 | |
| DW | 4 | m | ss | 8.1 | 24.9 | M | 63.4 | 11.2 | 21.7 | |
| JR | 16 | f | sbthal | 11.7 | 36.4 | H | 66.1 | 6.6 | 20.5 | |
| AS | 29 | f | ss | 7.2 | 21.5 | L | | | | |
| KP | 9 | f | sc | 10.9 | 33.7 | L | | | | |
| LT | 7 | m | sc | 11.4 | 35.1 | H | 28.7 | 37.9 | | 33.9 |
| SP | | f | sc | 11.1 | 33.1 | H | | | | |
| CS | | m | ss | 7.5 | 22.1 | L | | | | |
| Mean | 14.2 | | | 8.83 | 27.00 | | 73.16 | 15.45 | 22.50 | |

[a]Patient blood sample used in viscosity study discussed in Example 4.
[b]ss = homozygous HbS; sc = heterozygous HbS and HbC; sbthal = HbS with β-thalassemia chain.
[c]H = high dose, 6 mg/kg body weight; M = medium dose, 3 mg/kg body weight; L = low dose, 1.5 mg/kg body weight.

EXAMPLE 4
Viscosity Screening Method for APM Efficacy

The efficacy of APM treatment can be monitored by measuring the viscosity of patient blood samples before and after treatment. Normal blood viscosity increases with increasing hemoglobin concentration. While patients with sickle cell disease are anemic, the viscosity of their blood appears in the normal range; however, the viscosity is increased by an increase in the number of sickle cells relative to the number of normal cells.

Blood samples were obtained from ten patients having homozygous HbSS disease or heterozygous HbSC disease before and after a blinded administration of APM at 1.5 (low dosage), 3 (medium dosage), or 6 (high dosage) milligrams per kilogram body weight. The patients' characteristics are given in the first ten entries in Table II.

Viscosity determinations using the RBC pipette method of Wright and Jenkins (Wright, D. J. and Jenkins, Jr., D. E. 1970. *Blood* 36:516–522) were made on each blinded whole blood sample before and 120 minutes after blinded administration of APM. Each measurement was made in triplicate. Control viscosity measurements using saline and water for each patient and normal whole blood sample were also made to validate the viscosity measurements.

To measure viscosity, 1.01 cc of the test fluid, i.e., either water, saline or blood, was drawn into an RBC pipette using a 50 cc syringe attached via rubber tubing to the top of the RBC pipette. Using a constant pressure of 20 mm by maintaining the pressure with visual feedback and hand pressure, the amount of time it took for the test fluid to drip out of the RBC pipette was measured with a stopwatch. Each measurement was made in triplicate.

Figure 9:
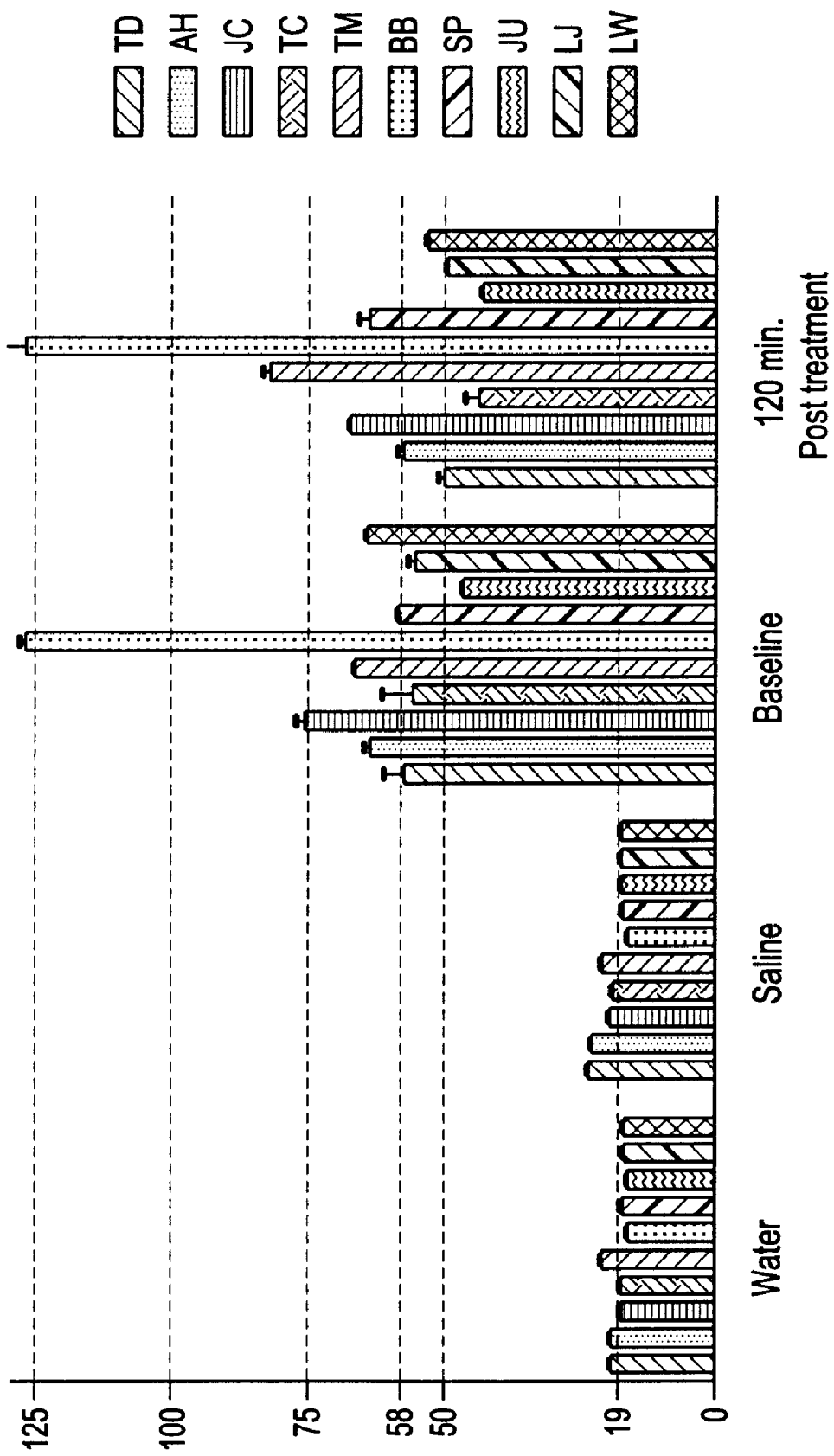
FIG. 9 is a graph depicting the viscosity measurements for each of the ten patient samples taken at baseline and 120 minutes post-APM administration. The first grouping is the concurrent measurement of the viscosity of water at the time and conditions under which the patient's blood sample was tested; the second grouping is the concurrent measurement of the viscosity of saline at the time and conditions under which the patient's blood sample was tested; the third grouping is the viscosity measurement for each patient taken at baseline (Time 0); and the fourth grouping is the viscosity measurement for each patient taken at 120 minutes post-treatment. In each grouping, the bars appear from left to right in the same order as the listings in the legend presented from top to bottom. The patients identified as TM, BB, and CH whose data is given in the respective 5th, 6th and 7th bar from the left in each treatment group had Hgbsc, or SC disease. The patient identified as TC whose data is given in the 4th bar from the left in each treatment group had sbthal disease. The other patients had sickle cell disease, or SS disease.

The results of the viscosity study obtained by comparing viscosity measurements obtained at baseline and 120 minutes post-treatment are summarized in FIG. 9 and Table III. Of the five patients identified as HgBss (homozygous for HbS), blood viscosity decreased after treatment over time. For the two patients diagnosed as sbthal (homozygous HbS with β-thalassemia chain), blood viscosity also decreased after treatment over time, resembling the results obtained with HgBss. In contrast, blood samples taken from three patients diagnosed as Hgbsc (heterozygous HbS and HbC) showed increased viscosity after treatment over time. According to this data, this method of monitoring can be used to delineate "sickle cell disease" from certain "sickle cell trait" disorders, e.g., Hgbsc. The viscosity data was also compared against Pirofsky's change in viscosity vs. hematocrit standard, and the results were that the viscosity decreased in blood samples from patients with sickle cell disease (HgBss) and increased in blood samples from patients with sickle cell trait (Hgbsc).

TABLE III

| | Viscosity results | | | |
|---|---|---|---|---|
| No. of Patients | Viscosity change | HgBss | sbthal | Hgbsc |
| 7 | decreasing | 5 | 2 | |
| 3 | increasing | | | 3 |

For comparative purposes, the number of sickle cells relative to the number of normal cells was obtained for each blinded sample before and 30, 60, 120, 240, and 1,440 minutes after blinded administration of APM using the metabisulfite test given in Example 1, with the exception that the ratio of metabisulfite to whole blood was 6:1, rather than 3:1.

Figure 10:
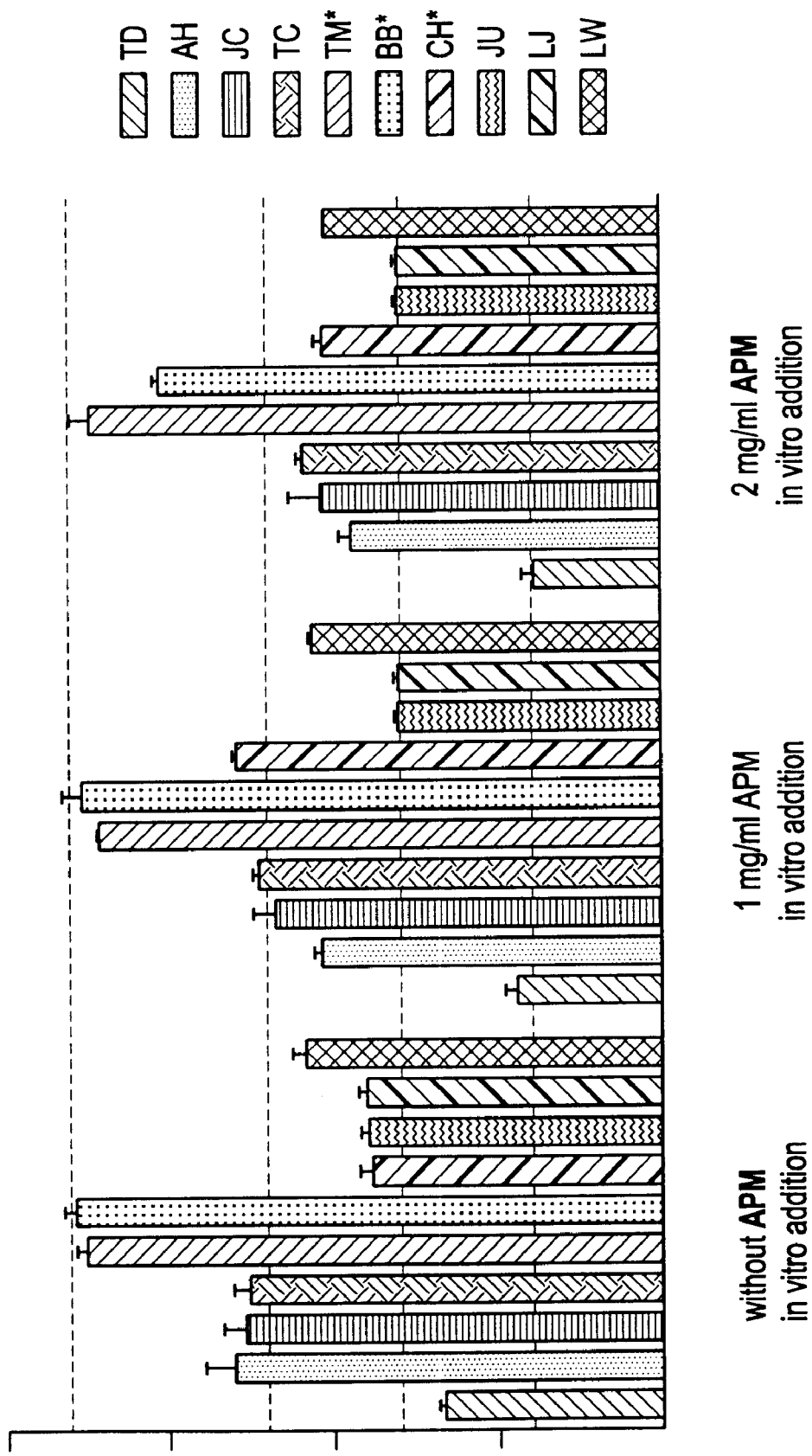
FIG. 10 is a graph depicting the viscosity measurements for each of the ten patient samples taken at 480 minutes post-in vivo APM treatment after the in vitro addition of 0, 1 milligram, or 2 milligrams of APM per milliliter. The first grouping was viscosity readings for patient samples measured at 480 minutes post-treatment to which no in vitro addition of APM was made; the second grouping was viscosity readings for patient samples measured at 480 minutes post-treatment to which 1 milligram per milliliter APM was added in vitro; and the third grouping was viscosity readings for patient samples measured at 480 minutes post-treatment to which 2 milligram per milliliter APM was added in vitro. In each grouping, the bars appear from left to right in the same order as the listings in the legend presented from top to bottom. The patients identified as TM, BB, and CH whose data is given in the respective 5th, 6th and 7th bar from the left in each treatment group had Hgbsc, or SC disease. The patient identified as TC whose data is given in the 4th bar from the left in each treatment group had sbthal disease. The other patients had sickle cell disease, or SS disease.

Samples with high viscosity readings at 480 minute or 1,440 minute posttreatment, chosen to represent patients with a validated response to APM who were returning to normal, were divided and treated with an additional 0, 1, or 2 milligrams/milliliter APM in vitro, in an effort to measure whether a second inducible sickling response was possible and if a second response to the in vitro APM addition could be observed. The viscosity of each sample at 480 minutes post-treatment was measured. As presented in FIG. 10, the viscosity of the blood samples from the patients classified as HgBss decreased over time when compared to the control. In contrast, blood samples from the Hgbsc patients showed an increase in viscosity over time compared to the control.

Baseline and 120 minute post-treatment viscosity measurements were compared with the number of sickle cells relative to the number of normal cells for correlation. A correlation was also made between the sickle cell count and viscosity, as shown in FIG. 11. The results demonstrated that as the number of sickle cells relative to the number of normal cells increased, the blood viscosity also increased in an essentially linearly proportional correlation.

APM given orally reduced the number of sickle cells in Hbss blood and also reduced the viscosity of HbSS blood. The addition of APM in vitro also reduced the number of sickle cells in HbSS blood and the viscosity of HbSS blood. The HbSC blood was not affected by APM in vivo or in vitro.

We claim:

1. A method for producing an antisickling effect in red blood cells in vitro comprising contacting said red blood cells with an effective amount of the compound

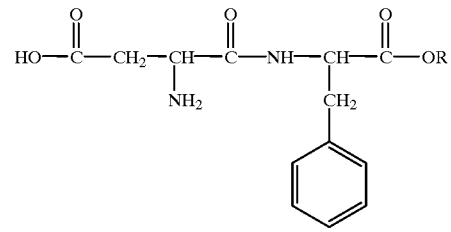

where R is $CH_3$ or an alkyl having 2 to 4 carbons.

2. The method of claim 1, wherein said effective amount of said compound is from 1 milligram to 2 milligrams per milliliter.

3. The method of claim 1 or 2, wherein R is $CH_3$.

4. A method for inhibiting the sickling of non-sickled red blood cells which may comprise hemoglobin S in vitro, comprising contacting said red blood cells with an effective amount of the compound

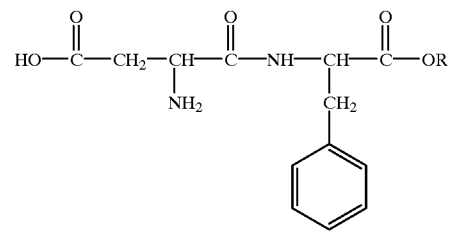

where R is $CH_3$ or an allyl having 2 to 4 carbons, wherein said effective amount inhibits the sickling of said non-sickled red blood cells.

5. The method of claim 4, wherein R is $CH_3$.

6. A method for reducing the number of sickled cells relative to the number of non-sickled red blood cells in a patient blood sample from the time of collection of said blood sample from said patient to a second time of laboratory analysis, comprising:

a. collecting a blood sample from a patient having a sickle cell disease, wherein said non-sickled red blood cells in said sample have a predisposition to sickle; and b. adding to said sample at we time of collection an effective amount of the compound

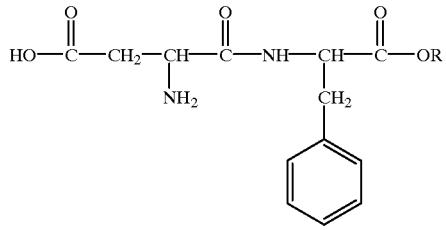

where R is CH₃ or an alkyl having 2 to 4 carbons, wherein said effective amount inhibits the sickling of said non-sickled red blood cells from the time of collection to the time of laboratory analysis.

7. The method of claim 6, wherein R is CH₃.

8. A method for treatment of sickle cell disease in a patient comprising administering to said patient an effective amount of the compound

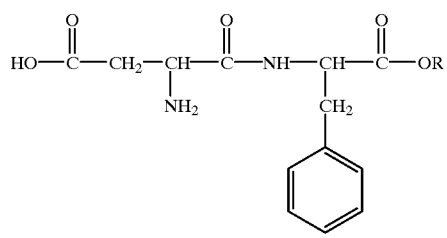

where R is CH₃ or an alkyl having 2 to 4 carbons to reduce the capacity of red blood cells in said patient to sickle.

9. The method of claim 8, wherein said effective amount is from 1.5 milligrams to 6 milligrams per kilogram body weight.

10. The method of claim 8, wherein said effective amount is 6 milligrams per kilograms body weight.

11. The method of claim 8, wherein R is CH₃.

12. The method of claim 9, wherein R is CH₃.

13. The method of claim 10, wherein R is CH₃.

14. The method of claim 8, 9, 10, 11, 12, or 13, wherein said effective amount is administered daily.

15. The method of claim 14, wherein said effective amount is administered orally.

* * * * *